United States Patent
Li et al.

(10) Patent No.: US 7,532,997 B2
(45) Date of Patent: May 12, 2009

(54) ELECTROMAGNETIC TRACKING USING A DISCRETIZED NUMERICAL FIELD MODEL

(75) Inventors: Dun Alex Li, Salem, NH (US); Peter Traneus Anderson, Andover, MA (US); Gerald Lee Beauregard, Stratham, NH (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/379,024

(22) Filed: Apr. 17, 2006

(65) Prior Publication Data

US 2007/0244666 A1    Oct. 18, 2007

(51) Int. Cl.
*G01C 17/00* (2006.01)

(52) U.S. Cl. .................. 702/150; 324/207.17; 702/134; 702/152

(58) Field of Classification Search .................. 702/150, 702/57, 94, 95, 104, 152, 153, 134; 324/207.16, 324/207.17, 207.18, 207.26; 342/463, 468
See application file for complete search history.

(56) References Cited

U.S. PATENT DOCUMENTS

| | | | |
|---|---|---|---|
| 3,121,228 A | 2/1964 | Kalmus | |
| 3,392,390 A | 7/1968 | Schelisch | |
| 3,529,682 A | 9/1970 | Coyne et al. | |
| 3,828,867 A | 8/1974 | Elwood | |
| 3,868,565 A | 2/1975 | Kulpers | |
| 3,983,474 A | 9/1976 | Kuipers | |
| 4,054,881 A | 10/1977 | Raab | |
| 4,176,662 A | 12/1979 | Frazer | |
| 4,314,251 A | 2/1982 | Raab | |
| 4,613,866 A | 9/1986 | Blood | |
| 4,618,822 A | 10/1986 | Hansen | |
| 4,622,644 A | 11/1986 | Hansen | |
| 4,642,786 A | 2/1987 | Hansen | |
| 4,710,708 A | 12/1987 | Rorden et al. | |
| 4,737,794 A | 4/1988 | Jones | |
| 4,742,356 A | 5/1988 | Kuipers | |
| 4,812,812 A | 3/1989 | Flowerdew et al. | |
| 4,820,041 A | 4/1989 | Davidson et al. | |
| 4,849,692 A | 7/1989 | Blood | |
| 4,945,305 A | 7/1990 | Blood | |
| 5,099,845 A | 3/1992 | Besz et al. | |

(Continued)

FOREIGN PATENT DOCUMENTS

WO     WO9811504    3/1998

OTHER PUBLICATIONS

Peter T. Anderson, "A Source of Accurately Calculable Quasi-Static Magnetic Fields," Ph.D. thesis, University of Vermont, Burlington, VT 05405, Oct. 2001.

(Continued)

*Primary Examiner*—John H Le (57) ABSTRACT

A method for electromagnetic tracking the position and orientation of an object using a discretized numerical field model, rather than the conventional analytical dipole model. The method including the steps of determining a discretized numerical field model associated with a particular distortion source; acquiring mutual inductance signals between electromagnetic sensors and the particular distortion source, the sensors being rigidly attached to a tracked object; estimating an initial position for the tracked object in the presence of the particular distortion source; refining the estimated position of the tracked object; and estimating an orientation of the tracked object.

19 Claims, 4 Drawing Sheets

U.S. PATENT DOCUMENTS

| | | | |
|---|---|---|---|
| 5,107,746 A | 4/1992 | Bauer |
| 5,172,056 A | 12/1992 | Voisin |
| 5,211,165 A | 5/1993 | Dumoulin et al. |
| 5,245,307 A | 9/1993 | Klaus et al. |
| 5,251,635 A | 10/1993 | Dumoulin et al. |
| 5,255,680 A | 10/1993 | Darrow et al. |
| 5,265,610 A | 11/1993 | Darrow et al. |
| 5,289,373 A | 2/1994 | Zarge et al. |
| 5,307,072 A | 4/1994 | Jones, Jr. |
| 5,307,808 A | 5/1994 | Dumoulin et al. |
| 5,377,678 A | 1/1995 | Dumoulin et al. |
| 5,425,367 A | 6/1995 | Shapiro et al. |
| 5,425,382 A | 6/1995 | Golden et al. |
| 5,437,277 A | 8/1995 | Dumoulin et al. |
| 5,443,066 A | 8/1995 | Dumoulin et al. |
| 5,445,150 A | 8/1995 | Dumoulin et al. |
| 5,453,686 A | 9/1995 | Anderson |
| 5,457,641 A | 10/1995 | Zimmer et al. |
| 5,517,195 A | 5/1996 | Narlow et al. |
| 5,558,091 A | 9/1996 | Acker et al. |
| 5,592,939 A | 1/1997 | Martinelli |
| 5,600,330 A | 2/1997 | Blood |
| 5,622,169 A | 4/1997 | Golden et al. |
| 5,640,170 A | 6/1997 | Anderson |
| 5,646,524 A | 7/1997 | Gilboa |
| 5,676,673 A | 10/1997 | Ferre et al. |
| 5,715,042 A | 2/1998 | Milani et al. |
| 5,767,669 A | 6/1998 | Hansen et al. |
| 5,782,765 A | 7/1998 | Jonkman |
| 5,800,352 A | 9/1998 | Ferre et al. |
| 5,803,089 A | 9/1998 | Ferre et al. |
| 5,829,444 A | 11/1998 | Ferre et al. |
| 5,847,976 A | 12/1998 | Lescourret |
| 5,873,822 A | 2/1999 | Ferre et al. |
| 5,913,820 A | 6/1999 | Bladen et al. |
| 5,953,683 A | 9/1999 | Hansen et al. |
| 5,967,980 A | 10/1999 | Ferre et al. |
| 6,052,610 A | 4/2000 | Koch |
| 6,073,043 A | 6/2000 | Schneider |
| 6,129,667 A | 10/2000 | Dumoulin et al. |
| 6,129,668 A | 10/2000 | Haynor et al. |
| 6,161,032 A | 12/2000 | Acker |
| 6,172,499 B1 | 1/2001 | Ashe |
| 6,175,756 B1 | 1/2001 | Ferre et al. |
| 6,177,792 B1 | 1/2001 | Govari et al. |
| 6,188,355 B1 | 2/2001 | Gilboa |
| 6,201,387 B1 | 3/2001 | Govari |
| 6,201,987 B1 | 3/2001 | Dumoulin |
| 6,203,493 B1 | 3/2001 | Ben-Haim |
| 6,211,666 B1 | 4/2001 | Acker |
| 6,223,066 B1 | 4/2001 | Govari |
| 6,226,547 B1 | 5/2001 | Lockhart et al. |
| 6,230,038 B1 | 5/2001 | von Gutfeld et al. |
| 6,233,476 B1 | 5/2001 | Strommer et al. |
| 6,246,231 B1 | 6/2001 | Ashe |
| 6,341,231 B1 | 1/2002 | Ferre et al. |
| 6,366,799 B1 | 4/2002 | Acker et al. |
| 6,369,564 B1 | 4/2002 | Khalfin et al. |
| 6,370,417 B1 | 4/2002 | Horbaschek et al. |
| 6,373,918 B1 | 4/2002 | Wiemker et al. |
| 6,374,131 B1 | 4/2002 | Tomita et al. |
| 6,374,134 B1 | 4/2002 | Bladen et al. |
| 6,377,041 B1 | 4/2002 | Jones, Jr. et al. |
| 6,400,139 B1 | 6/2002 | Khalfin et al. |
| 6,427,079 B1 | 7/2002 | Schneider et al. |
| 6,445,943 B1 | 9/2002 | Ferre et al. |
| 6,459,882 B1 | 10/2002 | Palermo et al. |
| 6,463,039 B1 | 10/2002 | Ricci et al. |
| 6,472,975 B1 | 10/2002 | Beigel et al. |
| 6,474,341 B1 | 11/2002 | Hunter et al. |
| 6,484,049 B1 | 11/2002 | Seeley et al. |
| 6,490,475 B1 | 12/2002 | Seeley et al. |
| 6,493,573 B1 | 12/2002 | Martinelli et al. |
| 6,516,213 B1 | 2/2003 | Nevo |
| 6,528,991 B2 | 3/2003 | Ashe |
| 6,534,982 B1 | 3/2003 | Jakab |
| 6,553,326 B1 | 4/2003 | Kirsch et al. |
| 6,584,301 B1 | 6/2003 | Bohn et al. |
| 6,624,626 B2 | 9/2003 | Khalfin |
| 6,625,563 B2 | 9/2003 | Kirsch et al. |
| 6,636,757 B1 | 10/2003 | Jascob et al. |
| 6,656,135 B2 | 12/2003 | Zogbi et al. |
| 6,667,612 B2 | 12/2003 | Duret |
| 6,701,179 B1 | 3/2004 | Martinelli et al. |
| 6,711,429 B1 | 3/2004 | Gilboa et al. |
| 6,754,596 B2 | 6/2004 | Ashe |
| 6,762,600 B2 | 7/2004 | Khalfin |
| 6,774,624 B2 | 8/2004 | Anderson et al. |
| 6,782,285 B2 | 8/2004 | Birkenbach et al. |
| 6,783,536 B2 | 8/2004 | Vilsmeier et al. |
| 6,784,660 B2 | 8/2004 | Ashe |
| 6,803,757 B2 | 10/2004 | Slates |
| 6,812,842 B2 | 11/2004 | Dimmer |
| 6,833,814 B2 | 12/2004 | Gilboa et al. |
| 6,836,745 B2 | 12/2004 | Seiler et al. |
| 6,838,873 B2 | 1/2005 | James et al. |
| 6,856,823 B2 | 2/2005 | Ashe |
| 6,856,826 B2 | 2/2005 | Seeley et al. |
| 6,856,827 B2 | 2/2005 | Seeley et al. |
| 6,947,788 B2 | 9/2005 | Gilboa et al. |
| 6,968,846 B2 | 11/2005 | Viswanathan |
| 6,980,921 B2 | 12/2005 | Anderson et al. |
| 6,995,729 B2 | 2/2006 | Govari et al. |
| 7,015,859 B2 | 3/2006 | Anderson |
| 2001/0045826 A1 | 11/2001 | Schneider |
| 2001/0047133 A1 | 11/2001 | Gilboa et al. |
| 2002/0035321 A1 | 3/2002 | Bucholz et al. |
| 2002/0045812 A1 | 4/2002 | Ben-Haim et al. |
| 2002/0049375 A1 | 4/2002 | Strommer et al. |
| 2002/0193685 A1 | 12/2002 | Mate et al. |
| 2003/0120150 A1 | 6/2003 | Govari |
| 2003/0184285 A1* | 10/2003 | Anderson et al. ...... 324/207.17 |
| 2003/0201767 A1 | 10/2003 | Khalfin |
| 2004/0011365 A1 | 1/2004 | Govari et al. |
| 2004/0019447 A1 | 1/2004 | Shachar |
| 2004/0068178 A1 | 4/2004 | Govari |
| 2004/0102696 A1 | 5/2004 | Govari |
| 2004/0129279 A1 | 7/2004 | Fabian et al. |
| 2004/0207389 A1 | 10/2004 | Nieminen et al. |
| 2004/0207528 A1 | 10/2004 | Fabian et al. |
| 2004/0210131 A1 | 10/2004 | Fukuda et al. |
| 2005/0003757 A1 | 1/2005 | Anderson |
| 2005/0004450 A1 | 1/2005 | Ben-Haim et al. |
| 2005/0012597 A1 | 1/2005 | Anderson |
| 2005/0015005 A1 | 1/2005 | Kockro |
| 2005/0049485 A1 | 3/2005 | Harmon et al. |
| 2005/0062469 A1 | 3/2005 | Anderson |
| 2005/0065433 A1 | 3/2005 | Anderson |
| 2005/0099290 A1 | 5/2005 | Govari |
| 2005/0107687 A1 | 5/2005 | Anderson |
| 2005/0165297 A1* | 7/2005 | Anderson et al. ........... 600/410 |
| 2005/0245821 A1 | 11/2005 | Govari et al. |
| 2005/0288574 A1 | 12/2005 | Thornton et al. |
| 2006/0025668 A1 | 2/2006 | Peterson et al. |
| 2006/0030771 A1 | 2/2006 | Levine et al. |
| 2006/0055712 A1 | 3/2006 | Anderson |
| 2006/0058604 A1 | 3/2006 | Avinash et al. |

OTHER PUBLICATIONS

B. K. P. Horn, "Closed-form solution of absolute orientation using unit quaternions," Journal of the Optical Society of America A, vol. 4, No. 4, pp. 629-642, Apr. 1987.

V. V. Kindratenko, "A survey of electromagnetic position tracker calibration techniques," Virtual Reality: Research, Development and Applications, vol. 5, No. 3, pp. 169-182, 2000.

Christopher Nafis, Vern Jensen, Lee Beauregard, and Peter Anderson, "Method for estimating dynamic EM tracking accuracy of surgical navigation tools," Proceedings of SPIE, vol. 6141, pp. 152-167, Medical Imaging 2006: Visualization, Image-Guided Procedures, and Display, Mar. 2006.

F. H. Raab, E. B. Blood, T. O. Steiner, and H. R. Jones, "Magnetic Position and Orientation Tracking System," IEEE Transactions on Aerospace and Electronic Systems, vol. AES—15, No. 5, pp. 709-718, Sep. 1979.

Tom Ahlkvist Scharfeld, "An Analysis of the Fundamental Constraints on Low Cost Passive Radio-Frequency Identification System Design," Master's thesis, Massachusetts Institute of Technology, Cambridge, MA 02139, Aug. 2001.

Ziou D et al: "Edge Detection Techniques—an Overview", Image Recognition Analysis Understanding and processing Techniques, Allen Press, Lawrence, KS, US, vol. 8, No. 4, 1998, pp. 537-559, XP008029269, ISSN: 1054-6618, section 3.3: "Edge Labeling": par. 1-3.

Robert Fisher et al: "Zero Crossing Detector", Image Processing Learning Resources, [Online] Jun. 2004, XP002424684 Internet: URL:http://web.archive.org/web/+/http://ho GO6T mepages. inf.ed. ac.uk/rbf/HIPR2/zeros.htm> [Mar. 13, 2007], section: "How It Works".

Huertas A et al: "Detection of Intensity Changes With Subpixel Accuracy Using Laplacian-Gaussian Masks", IEEE Transactions on Pattern Analysis and Machine Intelligence, IEEE Service Center, Los Alamitos, CA, US, vol. PAMI-8, No. 5, Sep. 1986, pp. 651-664, XP000857582, ISSN: 0162-8828.

Blaffert T et al: "The laplace integral for a watershed segmentation" 13,32 Image Processing, 2000. Proceedings. 2000 International Conference on Sep. 10-13, 2000, Piscataway, NJ, USA,IEEE, vol. 3, Sep. 10, 2000, pp. 444-447, XP010529499, ISBN: 0-7803-6297-7.

* cited by examiner

ELECTROMAGNETIC TRACKING USING A DISCRETIZED NUMERICAL FIELD MODEL

BACKGROUND

Electromagnetic trackers are sensitive to conductive or ferromagnetic objects. Presence of metallic targets near to an electromagnetic transmitter (Tx) or receiver (Rx) may distort the transmitting signals resulting inaccurate position and orientation (P&O) measurement.

Conventionally, there are varying approaches for recovering the distorted signals (or sensor P&O) for applications such that the sensor position is fixed relative to the surrounding metals. Indeed, the following reference shows many of the conventional approaches: V. V. Kindratenko, "A survey of electromagnetic position tracker calibration techniques", *Virtual Reality: Research, Development, and Applications*, pp. 169-182, Vol. 5, No. 3, 2000. The most popular approach is called "P&O mapping." With P&O mapping, the distortion is corrected by function-fitting the distorted P&O measurements to the undistorted counterparts based on a look-up table built on a desired tracking space.

The conventional approach of P&O mapping has proven to be a reliable solution for many applications, including fluoro-tracking applications. However, under the circumstance that the signals are significantly distorted (E.g., by conductive shield next to the sensor), the electromagnetic tracker may fail in processing the distorted signals and thus produce invalid P&O for distortion mapping. This largely degrades tracker performance and reliability.

Failure of the tracker in dealing with significant field distortion is primarily due to instability of conventional tracking algorithms. In conventional approaches, the directly-calculated P&O is optimized by using a fitting algorithm to best-fit the signal measurements to an analytical dipole model. Conventionally, the fitter tends to be very unstable in handling the measurements which are considerably deviated form the model predictions.

SUMMARY

Described herein are one or more implementations for electromagnetic tracking of position and orientation that utilizes a discretized numerical field model, rather than the conventional analytical dipole model.

This summary itself is not intended to limit the scope of this patent and the appending claims of this patent. Moreover, the title of this patent is not intended to limit the scope of this patent. For a better understanding of the present invention, please see the following detailed description and appending claims, taken in conjunction with the accompanying drawings. The scope of the present invention is pointed out in the appending claims.

BRIEF DESCRIPTION OF THE DRAWINGS

The same numbers are used throughout the drawings to reference like elements and features.

DETAILED DESCRIPTION

One or more implementations, described herein, are for electromagnetic (EM) tracking of position and orientation that utilizes a discretized numerical field model to compensate for EM field distortion. The conventional distortion-compensation approach employs the conventional analytical dipole model and is typically called position and orientation (P&O) mapping. The described implementations overcome the instability issues that the P&O mapping often has in dealing with significant field distortion. The described implementations also simplify conventional complex field distortion modeling.

The described implementations operate in the signal domain of measuring and modeling mutual inductance between an electromagnetic transmitter (Tx) and receiver (Rx). The numerical field model may be predetermined various ways, such as via robotic data acquisition process for the fluoro-navigation application or by double integral calculation where current segments are known with sufficient accuracy.

The described implementations also include seed searching and parameter fitting parts which both are conducted over a predetermined map of logarithm mutual inductance squared.

Exemplary EM Tracking System

Figure 1:
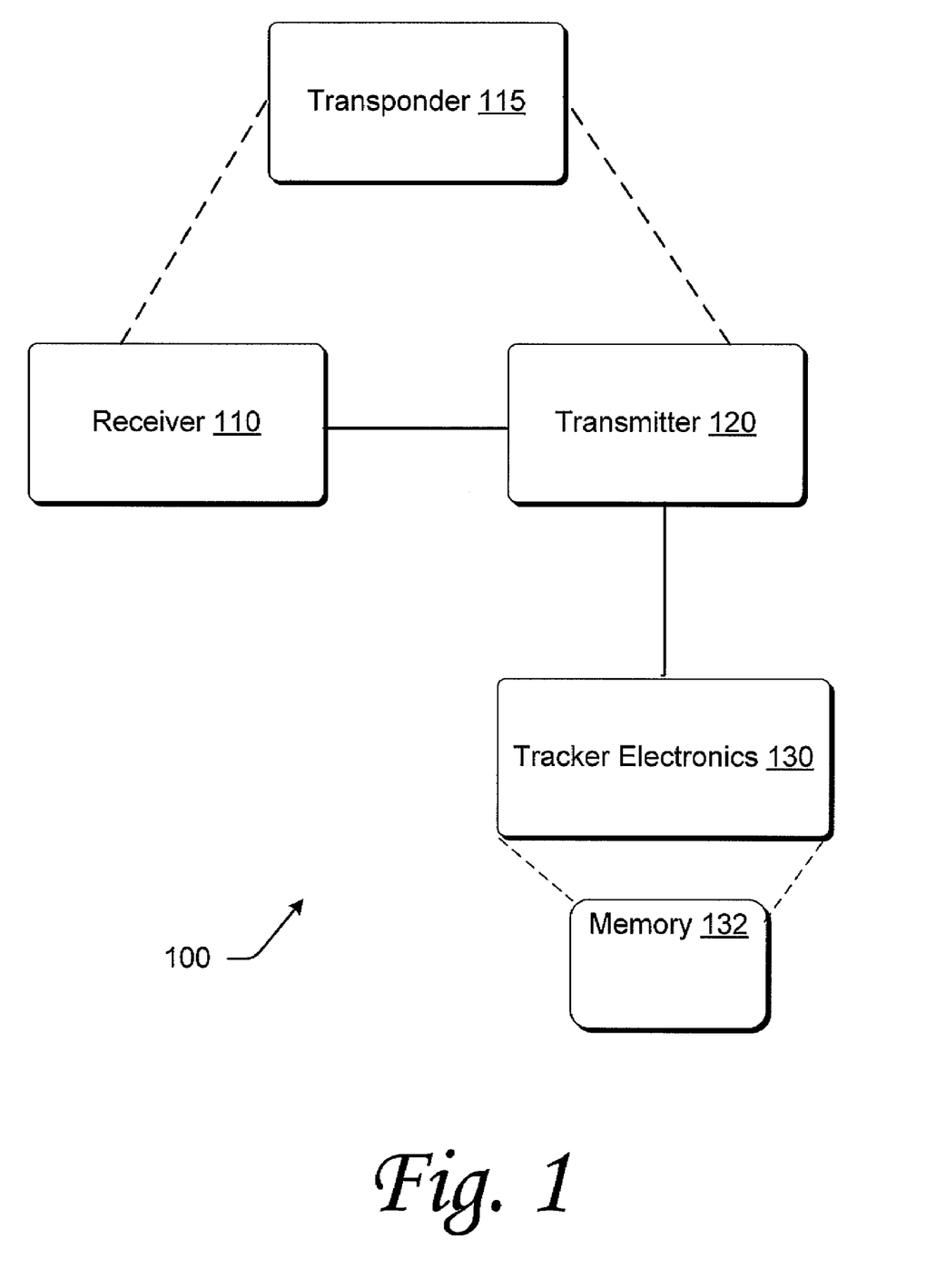
FIG. 1 shows an electromagnetic tracking system in accordance with one or more implementations described herein.

FIG. 1 illustrates an exemplary electromagnetic tracking system ("tracker") 100 used in accordance with one or more embodiments described herein. The tracker 100 includes a transmitter 110, a receiver 120, and tracker electronics 130. The tracker electronics 130 may be a computer or some other computational device. The various methods and procedures described herein are performed by the tracker electronics 130.

The tracker electronics 130 has at least one memory 132, which may be any available processor-readable media that is accessible by the tracker electronics 130. The memory 132 may be either volatile or non-volatile media. In addition, it may be either removable or non-removable media.

The transmitter 110 emits a transmitter signal. The receiver 120 detects the transmitter signal. The tracker electronics 130 analyzes the signals received by the receiver 120 and determine a position of the receiver 120.

Distortion-Compensation using the Conventional Analytical Dipole Model

The tracker 100 typically employs ISCA (Industry-standard Coil Architecture) 6-DOF (6 Degrees of Freedom) tracking technology. ISCA 6-DOF tracking typically includes a three-axis set of transmitter coils (denoted as txX, IxY, and txZ) which determine the coordinate system and a three-axis set of receiver coils (rx, rxY, and rxZ) to be tracked in the transmitter reference system. Typically, each transmitter coil is energized with a separate sinusoidal current $I_{tx}$ (at radian frequency ω) to create a time-varying magnetic field $B_{tx}$. The receiver coils pick up the transmitting signals producing measurable voltages induced by the $B_{tx}$ field.

According Faraday's law, the induced voltage $V_{rx}$ in the receiver coil is proportional to the rate of change of the magnetic flux $\Phi$ through the receiver coil loop, where the magnetic flux $\Phi$ is given by integrating the normal components of the $B_{tx}$ field over the coil loop.

$$V_{rx} = -\frac{d\Phi}{dt} = -\int\int j\omega \overline{B_{tx}} \cdot d\overline{A} \quad \text{Equation 1}$$

The ISCA receiver coils are small enough in comparing with Tx-Rx separating distance. The induced voltage $V_{rx}$ can be approximated as a dot product of the $B_{tx}$ field and the coil effective area vector $Aeff_{rx}$ or a scalar product of the normal component of the $B_{tx}$ field, $B_{tx\perp rx}$ and $Aeff_{rx}$ (magnitude of $Aeff_{rx}$).

$$V_{rx} = j\omega \overline{B_{tx}} \cdot \overline{Aeff_{rx}} = j\omega B_{tx\perp rx} \cdot Aeff_{rx} \qquad \text{Equation 2}$$

By measuring $V_{rx}$ and $Aeff_{rx}$, we can have the normal $B_{tx}$ field component for each receiver coil $$B_{tx\perp rx} = \frac{V_{rx}}{j\omega Aeff_{rx}} \qquad \text{Equation 3}$$

In ISCA tracker all three receiver coils are designed (or mathematically calibrated) to center on the same point and orthogonal to each other, measurements of three normal components of the $B_{tx}$ field, $B_{tx\perp rxX}$, $B_{tx\perp rxY}$, and $B_{tx\perp rxZ}$ essentially can be used to compose the field vector $$\overline{B_{tx}} = B_{tx\perp rxX} \cdot \hat{A} + B_{tx\perp rxY} \cdot \hat{B} + B_{tx\perp rxZ} \cdot \hat{C} \qquad \text{Equation 4}$$

where $\vec{A}, \vec{B}$, and $\vec{C}$ are unit vectors in directions of $Aeff_{rxX}$, $Aeff_{rxY}$, and $Aeff_{rxZ}$, respectively, defining the rotation of receiver coils with respect to the transmitter coils.

$$\overline{Aeff_{rxX}} = Aeff_{rx} \cdot \hat{A} \qquad \text{Equation 5}$$
$$\overline{Aeff_{rxY}} = Aeff_{rx} \cdot \hat{B}$$
$$\overline{Aeff_{rxZ}} = Aeff_{rx} \cdot \hat{C}$$

Considering all three magnetic fields, $B_{txX}$, $B_{txY}$, and $B_{txZ}$ created by transmitter coil txX, txY, and txZ, respectively, we have the corresponding measurements obtained by the three receiver coils expressed as $$\overline{B_{txX}} = B_{txX\perp rxX} \cdot \hat{A} + B_{txX\perp rxY} \cdot \hat{B} + B_{txX\perp rxZ} \cdot \hat{C} \qquad \text{Equation 6}$$
$$\overline{B_{txY}} = B_{txY\perp rxX} \cdot \hat{A} + B_{txY\perp rxY} \cdot \hat{B} + B_{txY\perp rxZ} \cdot \hat{C}$$
$$\overline{B_{txZ}} = B_{txZ\perp rxX} \cdot \hat{A} + B_{txZ\perp rxY} \cdot \hat{B} + B_{txZ\perp rxZ} \cdot \hat{C}$$

Note that the three magnetic fields $B_{txX}$, $B_{txY}$, and $B_{txZ}$ are only function of the position regardless of presence of the receiving coils. In traditional ISCA trackers, a relative simple dipole model was used to characterize the field distribution and track the receiver P&O in combination of measurements of the introduced signals in the coils. This is called the "analytical dipole model."

Distortion-Compensation Using the Discretized Numerical Field Model

However, the exemplary tracker 100 does not employ the conventional analytical dipole model for distortion-compensation. Instead, the exemplary tracker 100 employs a "discretized numerical field model." The discretized numerical field model is representation of spatially continuous EM field by a finite series of numerical field values.

Typically, the numerical model is pre-determined for a specific application (e.g., the receiver is rigidly attached to the fluoroscopy C-arm system). Once the discretized numerical field model is established within the desired tracking space, the model will precisely depict the magnetic field distribution in the specific application. Using this model improves the stability of the distortion correction. Ultimately a sensor's P&O may be accurately tracked using measurements directly acquired from any application.

The exemplary tracker 100 measures and models mutual inductance between transmitter and receiver coils. Just so that it is fully understood, the following shows that the measure of mutual inductance is effectively the same as the normal components of the $B_{tx}$ field for equations 1-6 discussed above.

The mutual inductance Lm is given by the ratio of the rate of change of current in the transmitter coil $I_{tx}$ and the induced voltage $V_{rx}$ in the receiver coil $$Lm = \frac{V_{rx}}{j\omega I_{tx}} \qquad \text{Equation 7}$$

which is very closely related to the transmitting field if we combine Equation 3 and Equation 7 ($I_{tx}$ and $Aeff_{rx}$ are known constants for specific transmitter and receiver combination)

$$Lm = \frac{Aeff_{rx}}{I_{tx}} \cdot B_{tx\perp rx} \qquad \text{Equation 8}$$

Similar to the expression of the transmitting $B_{tx}$ field in Equation 6, we may arrange the Lm measurement in a 3×3 matrix format where each element represents signal coupling between three transmitter coils (txX, txY, and txZ) and three receiver coils (rxX, rxY, and rxZ), respectively $$Lm = \begin{bmatrix} Lm^{[txX,rxX]} & Lm^{[txX,rxY]} & Lm^{[txX,rxZ]} \\ Lm^{[txY,rxX]} & Lm^{[txY,rxY]} & Lm^{[txY,rxZ]} \\ Lm^{[txZ,rxX]} & Lm^{[txZ,rxY]} & Lm^{[txZ,rxZ]} \end{bmatrix} \qquad \text{Equation 9}$$

The exemplary tracker 100 focuses on creating a numerical Lm model by either measuring or calculating (if analytical solutions are available) the mutual inductance matrix over a sampled space. More specifically, for the given metal distortion problem a robotic arm is used to move a transmitter to different nodes of a pre-specified sampling grid to record the distorted $Lm^{map}_i$ data with respect to the receiver which is rigidly attached to the fluoroscopy imaging intensifier. It is noted that electromagnetic transmitter and receiver are interchangeable according to the theory of reciprocity.

Henceforth, the Lm matrix and all related computation are conducted in the coordinate system defined by receiver. The corresponding undistorted transmitter P&O is also acquired in the receiver coordinates for each robot position i by removing the distorters such as the C-arm and electromagnetic shield from the proximity of receiver attachment. Alternatively, transmitter position can be obtained by only taking few tracker measurements to derive the translation and rotation coefficients between the tracker and robot coordinates, and later registering the robot position into tracker coordinate during distorted data collection.

Figure 2:
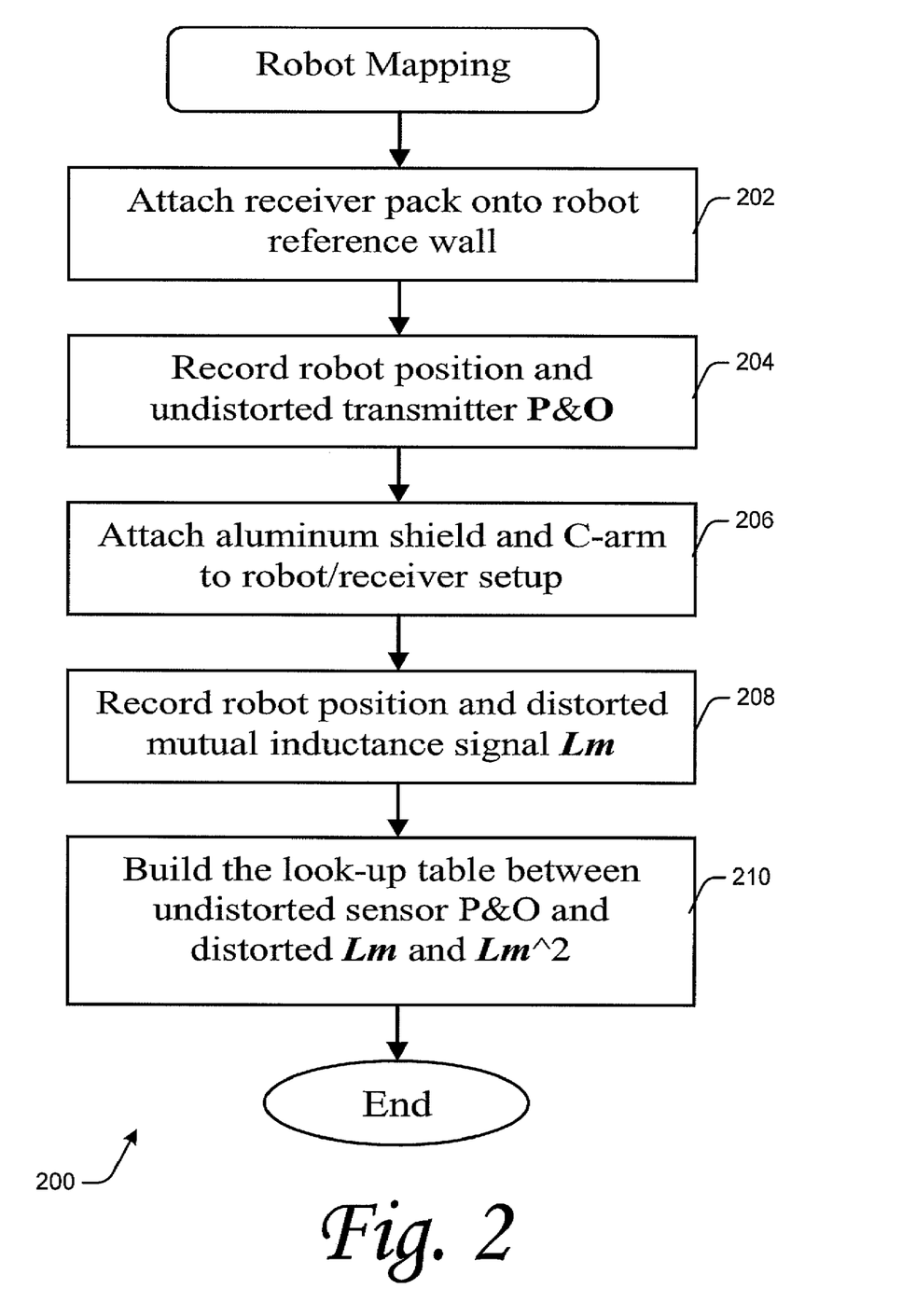
FIG. 2 shows a methodological implementation in accordance with one or more implementations described herein.

Methodological Implementation for the Acquiring Discretized Numerical Field Model FIG. 2 shows one method 200 for collecting measurements for construction of a discretized numerical field model for a particular distortion source. This method 200 is performed by the one or more of the various components by a robot enabled data collection system and process. Furthermore, this method 200 may be performed in software, hardware, or a combination thereof. For ease of understanding, this method is delineated as separate steps represented as independent blocks in FIG. 2; however, these separately delineated steps should not be construed as necessarily order dependent in their performance. Additionally, for discussion purposes, particular components are indicated as performing particular functions; however, other components (or combinations of components) may perform the particular functions.

At 202 of FIG. 2, a receiver is attached onto a reference wall fixed relative to the robot coordinate system.

At 204, the robot position is recorded as well as the undistorted transmitter P&O relative to the receiver.

At 206, a distortion source is attached to robot/receiver setup. A distortion source is a source of distortion which is to be measured and calculated. The distortion source may be, for example, a fluoroscopy C-arm. In other implementations, the distortion source may be something other than a C-arm such as a surgical table or microscope, etc.

At 208, with the to-be-measured distortion (e.g., the C-arm) in place, the robot position is recorded as well as the distorted mutual inductance signal Lm.

At 210, a look-up table is created. The table cross-references the undistorted sensor P&O and the distorted Lm and Lm^2. From Equation 9 with the data collected with the method of FIG. 2, the system may calculate distorted signals coupled from each of the transmitter coils to all three receiver coils in expression of mutual inductance squared $$Lm^{[rxX]}\!{}^{\wedge}2 = Lm^{[\alpha X, rxX]}\!{}^{\wedge}2 + Lm^{[\alpha Y, rxX]}\!{}^{\wedge}2 + Lm^{[\alpha Z, rxX]}\!{}^{\wedge}2$$

$$Lm^{[rxY]}\!{}^{\wedge}2 = Lm^{[\alpha X, rxY]}\!{}^{\wedge}2 + Lm^{[\alpha Y, rxY]}\!{}^{\wedge}2 + Lm^{[\alpha Z, rxY]}\!{}^{\wedge}2$$

$$Lm^{[rxZ]}\!{}^{\wedge}2 = Lm^{[\alpha X, rxZ]}\!{}^{\wedge}2 + Lm^{[\alpha Y, rxZ]}\!{}^{\wedge}2 + Lm^{[\alpha Z, rxZ]}\!{}^{\wedge}2 \quad \text{Equation 10}$$

Analogous to the magnetic fields, $Lm^2$ is independent of the transmitter orientation and is function of the transmitter position only. As a result, we can further express the mutual inductance (in logarithm in order to reduce the dynamic range) at any transmitter position $P(x_k, y_k, z_k)$ off the robot grid as a local polynomial interpolation of the tracker position $$\log(Lm_k^{rxX}\!{}^{\wedge}2) = c_{0X} + c_{1X}x_k + c_{2X}y_k + c_{3X}z_k + c_{4X}x_k^2 + c_{5X}y_k^2 + c_{6X}z_k^2 + c_{7X}x_ky_k + \ldots$$

$$\log(Lm_k^{rxY}\!{}^{\wedge}2) = c_{0Y} + c_{1Y}x_k + c_{2Y}y_k + c_{3Y}z_k + c_{4Y}x_k^2 + c_{5Y}y_k^2 + c_{6Y}z_k^2 + c_{7Y}x_ky_k + \ldots$$

$$\log(Lm_k^{rxZ}\!{}^{\wedge}2) = c_{0Z} + c_{1Z}x_k + c_{2Z}y_k + c_{3Z}z_k + c_{4Z}x_k^2 + c_{5Z}y_k^2 + c_{6Z}z_k^2 + c_{7Z}x_ky_k + \ldots \quad \text{Equation 11}$$

where $c_{0X}, c_{1X}, \ldots$ are coefficients of the polynomials computed from $Lm^{map}\!{}^{\wedge}2$ and undistorted transmitter position counterparts on a subset of sample nodes surrounding transmitter position $P(x_k, y_k, z_k)$. We may apply different polynomials—linear, quadratic, or cubic for the fitting. Usually the higher order polynomials the larger subset of $Lm^{map}$ measurements is required for estimate of the coefficients.

Once we have the complete representation of $Lm^{model}\!{}^{\wedge}2$ for the entire space of interest, the conventional analytical model is replaced in order to track the distorted transmitter P&O in the receiver reference system.

Methodological Implementation Using the Discretized Numerical Field Model

Figure 3:
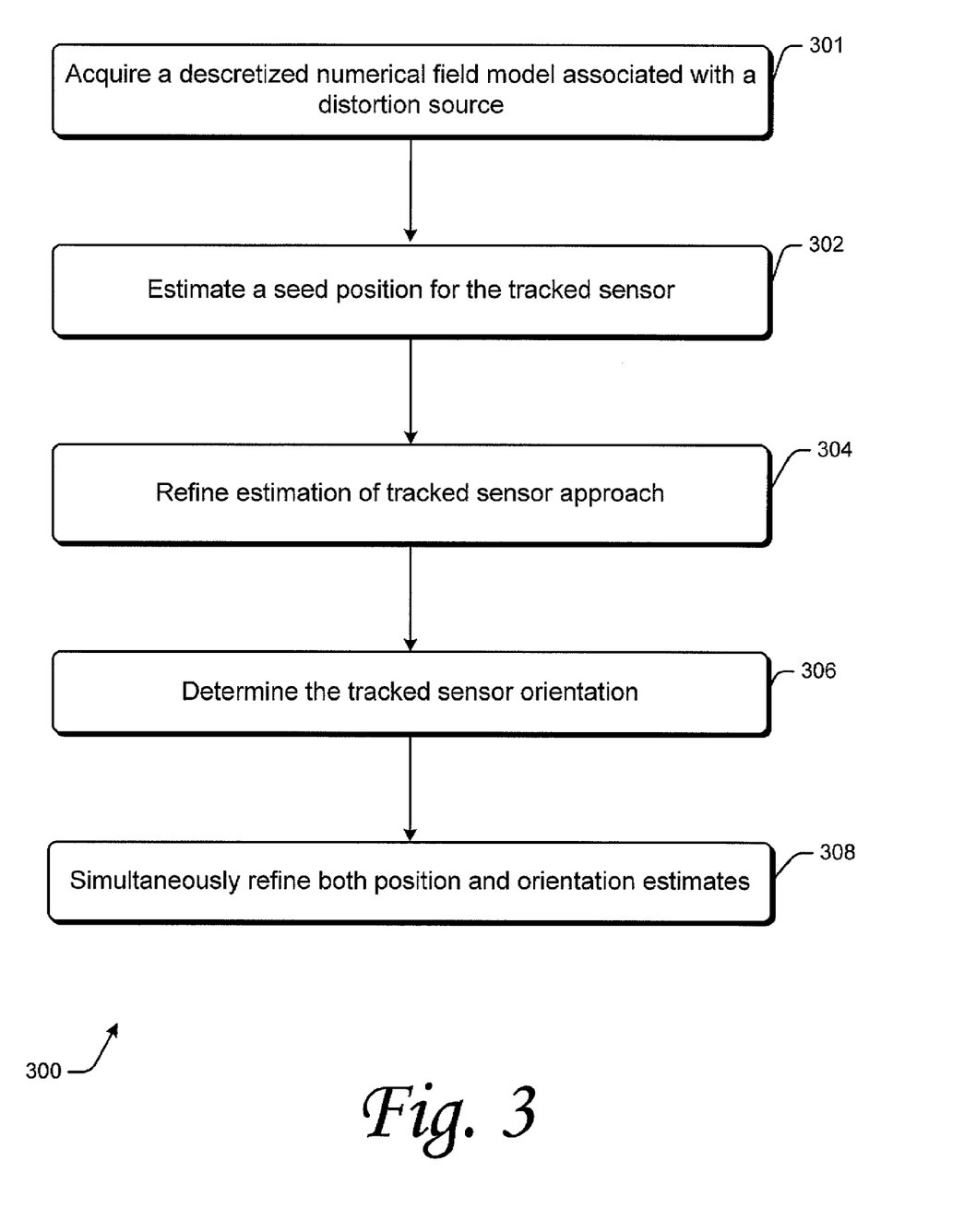
FIG. 3 shows a methodological implementation in accordance with one or more implementations described herein.

FIG. 3 shows a method 300 for EM P&O tracking using discretized numerical field model for a particular distortion source. This method 300 is performed by the one or more of the various components as depicted in FIG. 1. Furthermore, this method 300 may be performed in software, hardware, or a combination thereof. For ease of understanding, this method is delineated as separate steps represented as independent blocks in FIG. 3; however, these separately delineated steps should not be construed as necessarily order dependent in their performance. Additionally, for discussion purposes, the method 300 is described with reference to FIG. 1. Also for discussion purposes, particular components are indicated as performing particular functions; however, other components (or combinations of components) may perform the particular functions.

At 301 of FIG. 3, the discretized numerical field model associated with a particular distortion source is acquired. This is typically predetermined. The discretized numerical field model may be predetermined various ways, such as via robotic data acquisition process for the fluoroscopy-navigation application. The method 200 is an example of one way of acquiring discretized numerical field model for a particular distortion source by collecting and calculating data associated with the particular distortion source.

At 302, a seed position for the tracked sensor (e.g. a transmitter attached to the patient anatomy) is estimated within the presence of the same particular distortion source associated with the acquired discretized numerical field model. Assume that we have the mutual inductance measurement $Lm^{tracking}$ between the transmitter (to be tracked) and the receiver (permanently attached to the fluoro-system). We may compute the $Lm^{tracking}\!{}^{\wedge}2$ and monitor the difference from $Lm^{tracking}\!{}^{\wedge}2$ to each node of the $Lm^{map}\!{}^{\wedge}2$. The seed position will be the node in the map having the smallest $Lm^2$ difference $$\Delta = \|Lm^{tracking}\!{}^{\wedge}2 - Lm_i^{map}\!{}^{\wedge}2\| \quad \text{Equation 12}$$

where i is the index of the map node.

At 304 of FIG. 3, the estimate of the tracked sensor position is refined. This may be accomplished using an iterative fitting approach is used to create a best-fit of the measured mutual inductances $Lm^{tracking}\!{}^{\wedge}2$ to the estimated mutual inductances $Lm^{model}\!{}^{\wedge}2$ $$\frac{\partial[\log(Lm^{model}\,\wedge 2)]}{\partial P} \cdot \Delta P = [\log(Lm^{model}\,\wedge 2) - \log(Lm^{tracking}\,\wedge 2)] \quad \text{Equation 13}$$

The partial derivatives or the sensitivity matrix on the RHS (right-hand-side) of the equation is determined numerically from Equation 11. The sensor position is dynamically adjusted in every iteration until the difference (or so-called GOE—Goodness-of-fit) between measured and modeled data is within a certain tolerance.

$$P_{j+1} = P_j + \Delta P \quad \text{Equation 14}$$

where j is the iteration index.

Robustness of the fitter is mainly determined by the quality of the initial seed. For ISCA tracker, the fitter also tends to trap within local minima if any of the tracker coordinate values is close to zero. One approach is to mathematically rotate the coordinate system to move the position (expressed in Equation 9) far from the axes and calculate the tracker position in the rotated coordinate system and de-rotate the result back to the original coordinate.

Mathematically, the coordinate system is rotated to move both position estimate and the subset of $Lm^{map}$ used for calculating the $Lm^{model}$ to a region in which the numerical coordinates are substantially non-vanishing and the sensitivity matrix is well posed. Most of the rotations are performed in quaternion for each fitting iteration. The rotation quaternion is estimated from the updated sensor position. One way that this may be accomplished is described in U.S. Pat. No. 6,774,624. Equation 11 through Equation 14 are processed in the rotated coordinate system. Towards the end of the each fitting iteration, the updated sensor position will be de-rotated back to the original coordinate.

At 306, an estimate of the orientation of the tracked sensor is determined. Here, we need first to find out the rotation matrix $R^{distort}$ from the tracking D mutual inductance matrix $Lm^{tracking}$ to the model mutual inductance $Lm^{model}$ $$R^{distort} = \text{inverse}(Lm^{model}) \cdot Lm^{tracking} \qquad \text{Equation 15}$$

Rotation matrix $R^{distort}$ can be also expressed as a rotation quaternion $Q^{distort}$ for the rest of orientation calculation using methods described in Horn's paper. Due to the fact that the transmitter orientations remain constantly on the robot arm with respect to receiver during mapping data collection, $Lm^{model}$ can be obtained via a polynomial interpolation of the tracker position only $$Lm_k^m = c_{0m} + c_{1m}x_k + c_{2m}y_k + c_{3m}z_k + c_{4m}x_k^2 + c_{5m}y_k^2 + c_{6m}z_k^2 + c_{7m}x_ky_k + \ldots \qquad \text{Equation 16}$$

where m is the mth component of the $Lm_k$ matrix. $C_{0m}$, $C_{1m}$, ... are calculated from $Lm^{map}$ and transmitter position counterparts on the subset of sample nodes surrounding the estimated position.

To restore the undistorted sensor orientation, it is desirable to know the transmitter pose which is used for the mutual inductance mapping. Transmitter orientations are readily available from the undistorted P&O map. Since the transmitter is rigidly attached to the robot arm during data collection, its orientation should remain the same (denoted as $O^{map}$) for all map nodes as it is moved around to different robot locations. Thus, we have estimate for undistorted orientation $$O^{undistort} = O^{map} \cdot Q^{distort} \qquad \text{Equation 17}$$

If sufficient accuracy in position and orientation estimates is not achieved, then these estimate may be further refined by actions of block 308.

At 308 of FIG. 3, both position and orientation estimates are simultaneously refined by using a numerical fitter to best fit the measured mutual inductances $Lm^{tracking}$ to the estimated mutual inductances $Lm^{model} \cdot R^{distort}$. Because the transmitter orientation varies from different applications, the model $Lm^{model}$ should be aligned (by multiplying $Q^{distort}$) with $Lm^{tracking}$ prior to the least square fitting $$\left[ \frac{\partial(Lm^{model} \cdot R^{distort})}{\partial P} \frac{\partial(Lm^{model} \cdot R^{distort})}{\partial O} \right]$$

$$\left[ \begin{array}{c} \Delta P \\ \Delta O \end{array} \right] = [Lm^{model} \cdot R^{distort} - Lm^{tracking}] \qquad \text{Equation 18}$$

The partial derivatives on the RHS of the equation are determined numerically from Equation 11 and Equation 15. Both sensor position and orientation are dynamically adjusted in Equation 19 for all iterations until the difference between measured and modeled data is within a certain tolerance.

$$P_{j+1} = P_j + \Delta P$$

$$O_{j+1} = \Delta O \cdot O_j \qquad \text{Equation 19}$$

where j is the iteration index.

Seed Estimation

With the implementations disclosed herein, there is no analytical solution for initial tracker P&O estimation. Furthermore, because a local interpolation to the discretized field measurements is used to create the full numerical field model, low-quality initial seeds may result a large deviation from the model estimates to the measured signals. The fitter may either take many iterations to find the solution or fail completely without finding the global minima of the error. Therefore, it is desirable to have a robust seed searching approach.

This disclosed seed-searching approach herein does not require any knowledge of transmitter attachment pose on the patient anatomy thus demonstrates good flexibility for various navigation applications. This disclosed seed-searching approach is described in the context of electromagnetic navigation of a fluoro-imaging system where the position sensor is rigidly attached to the metallic part of the system and the transmitter is on the patient anatomy. However, it also can be applied to other applications such as wireless tracker.

Direct Seed-Searching

As we have shown above, the mutual inductance (denoted as Lm) measure is effectively identical to the normal components of the magnetic $BB_{rx}$ field. Consequently, a numerical Lm model is created by either measuring or calculating (if analytical solutions are available) the mutual inductance matrix over a sampled space.

The Lm measurement can be expressed in a 3×3 matrix format where each element represents signal coupling between three transmitter coils (txX, txY, and txZ) and three receiver coils (rxX, rxY, and rxZ), respectively as shown in Equation 9.

In order to remove Lm measurement dependency on transmitter or receiver coils, the measured Lm is normalized to the idealized Lm (e.g., perfectly concentric, orthogonal dipole with one square meter effective area). This may be accomplished using the approach described in U.S. Pat. No. 6,774,624, which is done by pre-multiplying the Lm by the receiver gain matrix inverse, and post-multiplying the inverse of the transmitter gain matrix.

In the given metal distortion problem, a robotic arm is used to move a transmitter to different nodes of a pre-specified sampling grid to record the distorted $Lm^{map}{}_i$ data with respect to the receiver which is rigidly attached to the fluoroscopy image intensifier. The corresponding undistorted transmitter P&O is also acquired in the receiver coordinates for each robot position i by removing the distorters such as the C-arm and electromagnetic shield from the proximity of receiver attachment.

From Equation 9, we can compute the distorted signals coupled from each of the transmitter coils to all three receiver coils in an expression of mutual inductance square as shown in Equation 10.

Analogous to the magnetic fields, the $Lm^2$ is independent of the transmitter orientation and is function of the transmitter position only. Thus, the seed problem is to map the $Lm^2$ to the transmitter position in the receiver coordinates.

Due to the symmetric of the dipole fields, the $Lm^2$ measurements are essentially the same for image positions in four quadrants of the receiver coordinates. Since the receiver is permanently attached to the fluoroscopy system, it is only allowed a designated clinical space (e.g. space right below the imaging intensifier) for the transmitter that is placed on patient anatomy. The first of seed estimation is to determine the hemisphere of the prospective tracking volume. This can be done by analyzing the undistorted P&O data collected during robot mapping process. The undistorted P&O data is processed by using the regular ISCA tracking algorithm. One such algorithm is described in U.S. Pat. No. 6,774,624. The hemisphere ambiguity is totally removed from tracker output.

Next, the sign of the three Lm^2 components in the predetermined tracker hemisphere is restored. Here we assume the clinical volume is always in the +z hemisphere of the receiver coordinates, which means the Lm^2 is always positive. The signs of $Lm^{[rxX]}\!{}^{\wedge}2$ and $Lm^{[rxY]}\!{}^{\wedge}2$ can be accomplished, respectively, using the polarities of the dot product of the mutual inductances $$\overline{Lm^{[rxZ]}} \bullet$$
$$\overline{Lm^{[rxZ]}} = Lm^{[\alpha X, rxZ]} \cdot Lm^{[\alpha X, rxX]} + Lm^{[\alpha Y, rxZ]} \cdot Lm^{[\alpha Y, rxX]} +$$
$$Lm^{[\alpha Z, rxZ]} \cdot Lm^{[\alpha Z, rxX]}$$

$$\overline{Lm^{[rxY]}} \bullet$$
$$\overline{Lm^{[rxZ]}} = Lm^{[\alpha X, rxY]} \cdot Lm^{[\alpha X, rxZ]} + Lm^{[\alpha Y, rxY]} \cdot Lm^{[\alpha Y, rxZ]} +$$
$$Lm^{[\alpha Z, rxY]} \cdot Lm^{[\alpha Z, rxZ]} \qquad \text{Equation 20}$$

Therefore, $$Lm_{\pm}^{[rxX]}\!{}^{\wedge}2 = \text{sign}(\overline{Lm^{[rxZ]}} \bullet \overline{Lm^{[rxX]}}) \cdot Lm^{[rxX]}\!{}^{\wedge}2$$

$$Lm_{\pm}^{[rxY]}\!{}^{\wedge}2 = \text{sign}(\overline{Lm^{[rxY]}} \bullet \overline{Lm^{[rxZ]}}) \cdot Lm^{[rxY]}\!{}^{\wedge}2$$

$$Lm_{\pm}^{[rxZ]}\!{}^{\wedge}2 = +Lm^{[rxZ]}\!{}^{\wedge}2 \qquad \text{Equation 21}$$

Assume that we have the mutual inductance measurement $Lm^{tracking}$ between the transmitter (to be tracked) and the receiver (permanently attached to the fluoro-system) taken during patient scan. We may compute the $Lm_{\pm}^{tracking}\!{}^{\wedge}2$ and monitor the difference from $Lm_{\pm}^{tracking}\!{}^{\wedge}2$ to each node of the $Lm_{\pm}^{map}\!{}^{\wedge}2$. In theory, the seed position shall be the node in the map with the smallest $Lm_{\pm}^{\wedge}2$ difference $$\Delta = \|\overline{Lm_{\pm}^{tracking}\!{}^{\wedge}2} - \overline{Lm_{\pm}^{mapi}\!{}^{\wedge}2}\| \qquad \text{Equation 22}$$

where i is the index of the map node.

For ISCA tracker, however, this direct seed-searching approach may experience numerical instability issue if any of the tracker coordinate values is close to zero. This can be avoided by mathematically rotating the coordinate system to move the position far from the axes, calculating the tracker position in the rotated coordinate system, and then mathematically de-rotating the result back to the original coordinate.

Methodological Implementation for Seed Estimation

Figure 4:
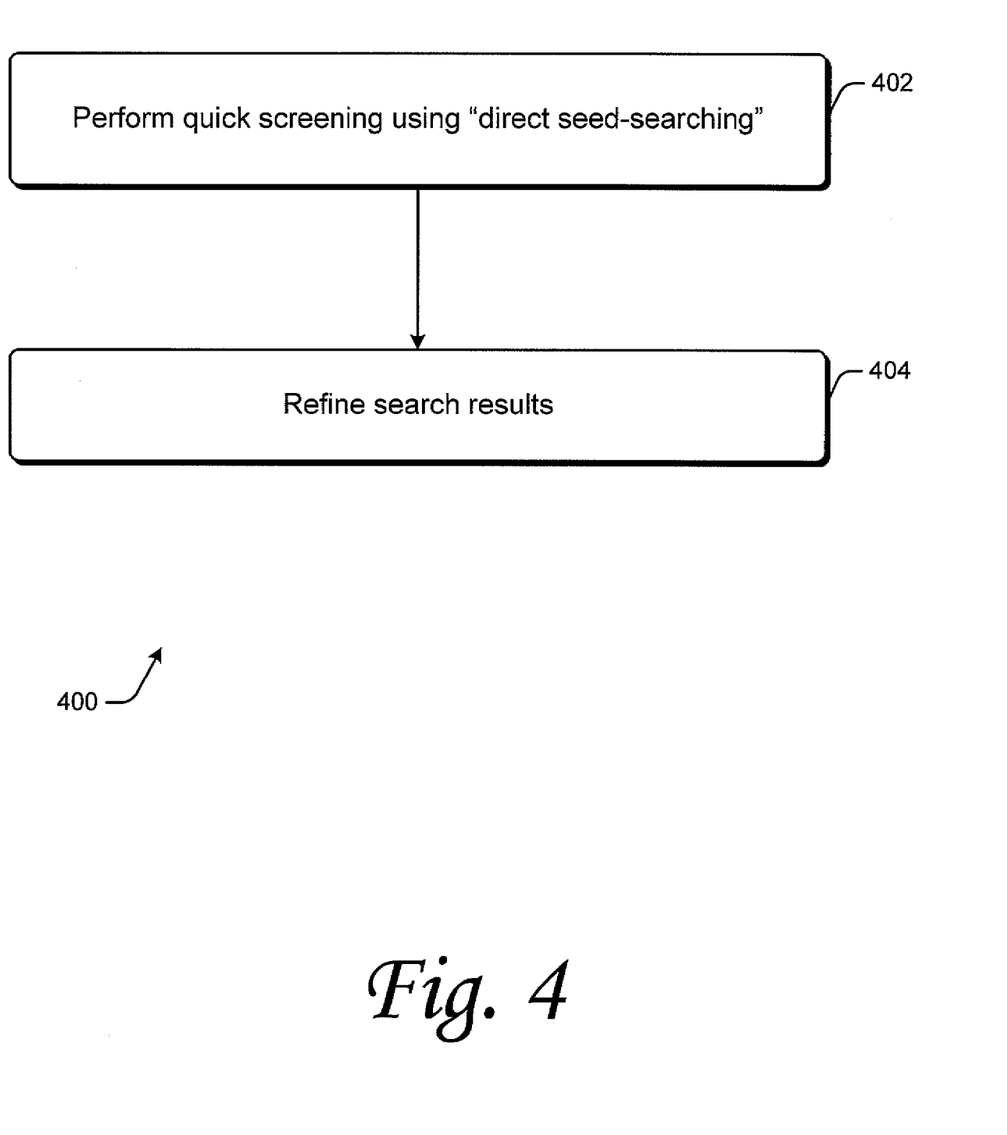
FIG. 4 shows a methodological implementation in accordance with one or more implementations described herein.

FIG. 4 shows a method 300 for estimating for the initial seed. This method 400 is an elaboration on the action taken at 302 of FIG. 3. This method 400 is performed by the one or more of the various components as depicted in FIG. 1. Furthermore, this method 400 may be performed in software, hardware, or a combination thereof. For ease of understanding, this method is delineated as separate steps represented as independent blocks in FIG. 4; however, these separately delineated steps should not be construed as necessarily order dependent in their performance. Additionally, for discussion purposes, the method 400 is described with reference to FIG. 1. Also for discussion purposes, particular components are indicated as performing particular functions; however, other components (or combinations of components) may perform the particular functions.

At 402 of FIG. 4, a quick screening is performed which a "direct seed-searching approach" described above.

At 404, the search result are refined. To do this, we empirically choose a subset (10 to 20 data points) of the $Lm_{\pm}^{map}\!{}^{\wedge}2$ map based on the output form Equation 5, which has the smallest distance to $Lm_{\pm}^{tracking}\!{}^{\wedge}2$. Then we extract the corresponding undistorted tracker position, $P_j$ and mutual inductance measurement, $Lm_j^{map}$ from the map data sets collected by the robot system, where j=1, 2, . . . 20 denotes the index of the data points in the subset. For each data position $P_j$, one can calculate the unit vector located in the same quadrant as the $P_j$ does but having identical scalar components on the three axes $$\hat{\vec{V}}_j = \frac{\text{sign}(\vec{P}_j)}{\sqrt{3}} \qquad \text{Equation 23}$$

A quaternion vector, $Q_{rotj}$ grow which represents the rotation from unit vector $\vec{P}_j$ to $\vec{V}_j$ is then computed. The following step is to mathematically rotate the coordinate system to move both the $Lm_j^{map}$ and $Lm^{tracking}$ to a region in which the numerical coordinates are substantially non-vanishing and the sensitivity matrix is well posed. To do this, we apply the same rotation quaternion $Q_{rotj}$ to both $Lm_j^{map}$ and $Lm^{tracking}$ and re-estimate the difference between $Lmrot_j^{map}$ and $Lmrot^{tracking}$ in the rotated coordinate system.

$$\Delta_{rot} = \|\overline{Lmrot_{\pm}^{tracking}\!{}^{\wedge}2} - \overline{Lmrot_{\pm}^{mapj}\!{}^{\wedge}2}\| \qquad \text{Equation 24}$$

The rotation should not change the actual distance between any two vectors located in the same coordinate system. For the on-axis Lm measurements, however, the reassessment of the $Lm_j^{map}$ and $Lm^{tracking}$ distance in a numerically "friendly" coordinates may significantly improve the stability of the approach for accurate seed estimation.

Other Applications, Implementations, and Details

The discussion herein focuses on the specifics of a medical tracking or navigational system, especially on used to track medical instruments in a patient's anatomy. However, the details of these described specifics are merely exemplary. The described implementations are particularly useful in both real-time and intensive EM field computation.

The focus of at least one of the described implementations for electromagnetic navigation of fluoroscopy system where the receiver is rigidly attached to the metallic part of the system and transmitter is on the patient anatomy. However, other implementations may also be applied to other application such as a wireless tracker.

The functionality of the described implementations may and can be employed in variety of applications where it is desirable to accurately track the position of items other than medical instruments in a variety of applications. That is, a tracking system may be used in other settings where the position of an instrument in an object or an environment is difficult to accurately determine by visual inspection.

Recall that, by reciprocity, the mutual inductance of two coils is the same, whichever coil is the transmitter and which is the receiver. Therefore, unless the context indicates otherwise, the reader should understand that when transmitters and receivers are discussed herein, the relative positioning and functionality of the receivers and transmitters may be swapped. Because of mutual inductance the functionality of the implementation with swapped receivers and transmitters remains the same as an implementation where there is no swapping of the receivers and transmitters.

Furthermore, the techniques, described herein, may be implemented in many ways, including (but not limited to) medical devices, medical systems, program modules, general- and special-purpose computing systems, network servers and equipment, dedicated electronics and hardware, and as part of one or more computer networks.

Although the one or more above-described implementations have been described in language specific to structural features and/or methodological steps, it is to be understood that other implementations may be practiced without the specific features or steps described. Rather, the specific features and steps are disclosed as preferred forms of one or more implementations.

The invention claimed is:

1. A method for electromagnetic tracking, the method comprising:
   determining a discretized numerical field model associated with a particular distortion source;
   acquiring mutual inductance signals between electromagnetic sensors and the particular distortion source, the sensors being rigidly attached to a tracked object;
   estimating an initial position for the tracked object in the presence of the particular distortion source;
   refining the estimated position of the tracked object; and
   estimating an orientation of the tracked object.

2. The method as recited in claim 1, further comprising simultaneously refining estimates of both position and orientation.

3. The method as recited in claim 1, wherein the refining is performed iteratively.

4. The method as recited in claim 1, wherein the estimating an initial position comprises direct seed-searching and refining results of the direct seed-searching.

5. The method as recited in claim 1, wherein the particular distortion source is comprises a C-arm of a fluoroscope, a surgical table, surgical equipment, or other surgical instrument.

6. The method as recited in claim 1, wherein the acquiring further comprises generating the discretized numerical field model associated with the particular distortion source.

7. The method as recited in claim 6, wherein the generating comprises:
   measuring "undistorted" sensor position and orientation at multiple positions and orientations in an designated volume without the presence of the particular distortion source;
   measuring "distorted" mutual inductance between electromagnetic sensors at multiple positions and orientations in the same designated volume with the presence of the particular distortion source; and
   mapping the "undistorted" sensor position and orientation and the "distorted" mutual inductance between electromagnetic sensors.

8. A method for electromagnetic tracking, the method comprising:
   determining a discretized numerical field model associated with a particular distortion source;
   acquiring mutual inductance signals between electromagnetic sensors and the particular distortion source, the sensors being rigidly attached to a tracked object;
   estimating an initial position for the tracked object in the presence of the particular distortion source;
   refining the estimated position of the tracked object; and
   estimating an orientation of the tracked object;
   wherein the estimating an initial position comprises direct seed-searching and refining results of the direct seed-searching, wherein the direct seed-searching comprises:
   generating an orientation-independent mutual-inductance squared vector map ("mapped $Lm^2$") based on acquired mutual inductance measurements associated with the particular distortion source;
   measuring the acquired mutual inductance signals between the electromagnetic sensors and the particular distortion source;
   computing mutual-inductance squared vector $Lm^2$ of the tracked object;
   determining which hemisphere contains positional ("x, y, and z") components of the $Lm^2$ of the tracked object;
   computing the difference from the $Lm^2$ to each node of the mapped $Lm^2$; and
   using, as the direct seed, the node position in the mapped $Lm^2$ having the smallest $Lm^2$ difference.

9. A computer-readable media having computer-executable instructions thereon that, when executed by a computer, perform a method for electromagnetic tracking, the method comprising:
   determining a discretized numerical field model associated with a particular distortion source;
   acquiring mutual inductance signals between electromagnetic sensors and the particular distortion source, the sensors being rigidly attached to a tracked object;
   estimating an initial position for the tracked object in the presence of the particular distortion source;
   refining the estimated position of the tracked object; and
   estimating an orientation of the tracked object.

10. The computer-readable media as recited in claim 9, further comprising simultaneously refining estimates of both position and orientation.

11. The computer-readable media as recited in claim 9, wherein the refining is performed iteratively.

12. The computer-readable media as recited in claim 9, wherein the particular distortion source comprises a C-arm of a fluoroscope, a surgical table, surgical equipment, or other surgical instrument.

13. The computer-readable media as recited in claim 9, wherein the acquiring further comprises generating the discretized numerical field model associated with the particular distortion source.

14. The computer-readable media as recited in claim 13, wherein the generating comprises:
   measuring "undistorted" sensor position and orientation at multiple positions and orientations in an designated volume without the presence of the particular distortion source;
   measuring "distorted" mutual inductance between electromagnetic sensors at multiple positions and orientations in the same designated volume with the presence of the particular distortion source; and
   mapping the "undistorted" position and the "distorted" mutual inductance between electromagnetic sensors.

15. A method for electromagnetic tracking, the method comprising:
   determining a discretized numerical field model associated with a particular distortion source;
   acquiring mutual inductance signals between electromagnetic sensors and the particular distortion source, the sensors being rigidly attached to a tracked object;
   measuring a "distorted" mutual inductance between the electromagnetic sensors in the presence of the particular distortion source; and
   compensating for distortion caused by the particular distortion source by adjusting the measured "distorted"

position and orientation for the tracked object, wherein the compensation is based upon the acquired discretized numerical field model.

16. The method as recited in claim 15, wherein the compensating comprises:
estimating a initial position for the tracked object in the presence of the particular distortion source;
refining the estimated position of the tracked object; and
estimating an orientation of the tracked object.

17. The method as recited in claim 15, wherein the acquiring further comprises generating the discretized numerical field model associated with the particular distortion source.

18. The method as recited in claim 15, wherein the particular distortion source is comprises a C-arm of a fluoroscope, a surgical table, surgical equipment, or other surgical instrument.

19. A method for electromagnetic tracking, the method comprising:
determining a discretized numerical field model associated with a particular distortion source;
acquiring mutual inductance signals between electromagnetic sensors and the particular distortion source, the sensors being rigidly attached to a tracked object;
measuring a "distorted" mutual inductance between the electromagnetic sensors in the presence of the particular distortion source; and
compensating for distortion caused by the particular distortion source by adjusting the measured "distorted" position and orientation for the tracked object, wherein the compensation is based upon the acquired discretized numerical field model;
wherein the compensating comprises:
estimating a initial position for the tracked object in the presence of the particular distortion source;
refining the estimated position of the tracked object; and
estimating an orientation of the tracked object;
wherein the estimating an initial position comprises direct seed-searching and refining results of the direct seed-searching, wherein the direct seed-searching comprises:
generating an orientation-independent mutual-inductance squared vector map ("mapped $Lm^2$") based on acquired mutual inductance measurements associated with the particular distortion source;
measuring the acquired mutual inductance signals between the electromagnetic sensors and the particular distortion source;
computing mutual-inductance squared vector $Lm^2$ of the tracked object;
determining which hemisphere contains positional ("x, y, and z") components of the $Lm^2$ of the tracked object;
computing the difference from the $Lm^2$ to each node of the mapped $Lm^2$; and
using, as the direct seed, the node position in the mapped $Lm^2$ having the smallest $Lm^2$ difference.

\* \* \* \* \*